United States Patent
Cohen

(10) Patent No.: US 6,489,534 B1
(45) Date of Patent: Dec. 3, 2002

(54) DISPOSABLE PERSONAL ARTICLES WHICH CONFORM AND ADHERE

(75) Inventor: Bernard Cohen, Duluth, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/561,994

(22) Filed: Apr. 28, 2000

(51) Int. Cl.$^7$ ................................................ A61F 13/15
(52) U.S. Cl. .................. 604/367; 604/372; 604/385.03; 604/389; 604/367; 428/68; 602/57
(58) Field of Search ................. 604/367, 385.03, 604/389, 57; 428/68; 602/57

(56) References Cited

U.S. PATENT DOCUMENTS

| | | | |
|---|---|---|---|
| 3,389,827 A | 6/1968 | Abere et al. | 220/53 |
| 4,693,776 A | 9/1987 | Krampe et al. | 156/327 |
| 4,716,208 A | 12/1987 | Korzeniowski | |
| 4,732,808 A | 3/1988 | Krampe et al. | 428/355 |
| 4,753,648 A * | 6/1988 | Jackson | 604/389 |
| 5,088,483 A | 2/1992 | Heinecke | 602/46 |
| 5,103,812 A | 4/1992 | Salamone et al. | 602/52 |
| 5,270,111 A | 12/1993 | D'Haese et al. | 428/356 |
| 5,520,629 A | 5/1996 | Heinecke et al. | 602/57 |
| 5,591,820 A | 1/1997 | Kydonieus et al. | 528/76 |
| 5,599,289 A * | 2/1997 | Castellana | 602/57 |
| 5,613,942 A | 3/1997 | Lucast et al. | 602/52 |
| 5,641,844 A | 6/1997 | Thompson et al. | 526/245 |
| 5,820,973 A | 10/1998 | Dodge, II et al. | 428/212 |
| 5,879,343 A | 3/1999 | Dodge, II et al. | 604/378 |
| 5,957,126 A | 9/1999 | Neeser | 128/200.24 |
| 6,068,852 A | 5/2000 | Shah | 424/443 |

FOREIGN PATENT DOCUMENTS

| | | | |
|---|---|---|---|
| EP | 0 234 724 | 9/1987 | |
| FR | 99/06495 | 2/1999 | ......... C09D/133/16 |
| WO | 98/27909 | 7/1998 | ......... A61F/13/15 |
| WO | 98/27910 | 7/1998 | ......... A61F/13/15 |
| WO | 98/27911 | 7/1998 | ......... A61F/13/15 |
| WO | 98/27912 | 7/1998 | ......... A61F/13/15 |
| WO | 98/27913 | 7/1998 | ......... A61F/13/15 |
| WO | 98/27914 | 7/1998 | ......... A61F/13/15 |
| WO | 98/27915 | 7/1998 | ......... A61F/13/15 |
| WO | 98/27916 | 7/1998 | ......... A61F/13/15 |
| WO | 98/27917 | 7/1998 | ......... A61F/13/15 |
| WO | 98/27918 | 7/1998 | ......... A61F/13/15 |
| WO | 98/28015 | 7/1998 | ......... A61L/15/58 |
| WO | 98/28017 | 7/1998 | ......... A61L/15/58 |
| WO | 99/01094 | 1/1999 | ......... A61F/13/15 |
| WO | 99/06495 | 2/1999 | ......... C09D/133/16 |
| WO | 00/00124 | 1/2000 | ......... A61F/13/15 |
| WO | 00/00132 | 1/2000 | ......... A61F/13/15 |
| WO | 00/07636 | 2/2000 | ......... A61L/15/58 |
| WO | 00/07637 | 2/2000 | ......... A61L/15/58 |
| WO | 00/24350 | 5/2000 | ......... A61F/13/15 |

\* cited by examiner

Primary Examiner—Rodney M. Lindsey
Assistant Examiner—Angela J Grayson
(74) Attorney, Agent, or Firm—Steven D. Flack

(57) ABSTRACT

There is provided a disposable personal article with a polymer having a glass transition temperature ranging between 25 and 45° C. The polymer is tacky over the temperature range, which is approximately that of the body, and results in better sealing of the personal care product to the wearer and so a decrease in the amount of bodily exudates that escape to soil the clothing of a wearer. The preferred polymer has a main chain, lateral perfluoroalkyl groups and lateral alkyl groups.

13 Claims, 1 Drawing Sheet

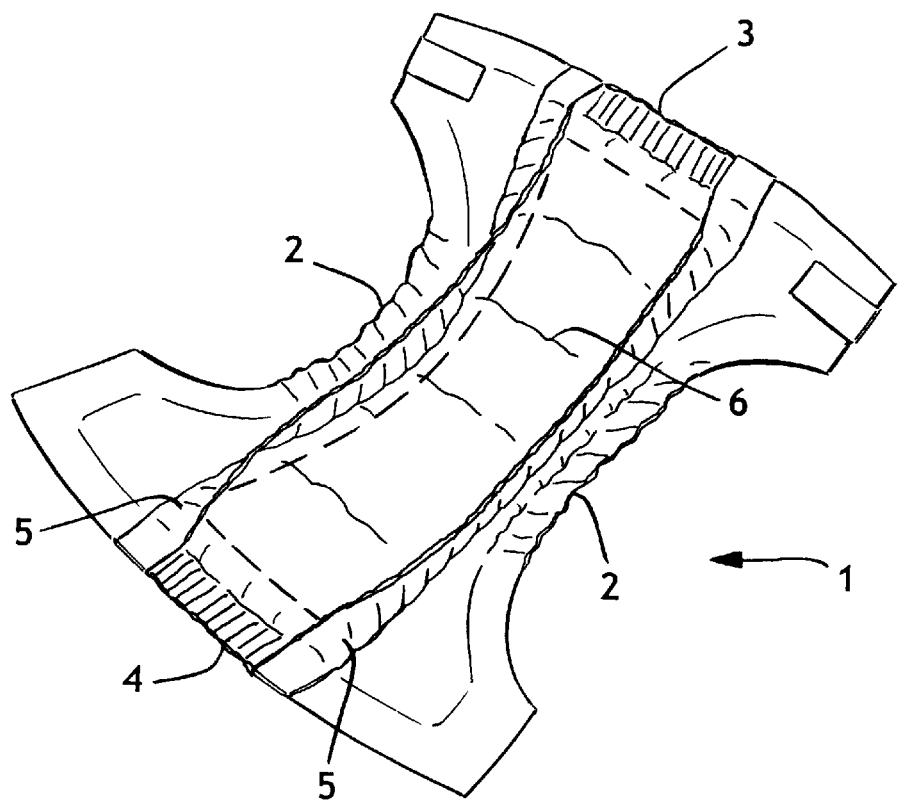

DISPOSABLE PERSONAL ARTICLES WHICH CONFORM AND ADHERE

FIELD OF THE INVENTION

The invention is related primarily to personal care products and may also be applied to some medical products. More particularly, it concerns disposable personal articles such as feminine care napkins, diapers and training pants, swimwear, wound care dressings and bandages, facemasks, and adult incontinence products, that conform and adhere to the body of the wearer.

BACKGROUND OF THE INVENTION

Disposable personal care products typically are made with a top sheet material (also referred to as a cover sheet or liner) an absorbent core and a liquid impermeable back sheet. Some may also have a surge layer or other specialized layers between the top sheet and absorbent core.

Personal care products generally have parts with sealing surfaces that are adapted to hold the product against the wearer to reduce leakage. Such parts may be referred to as "leg cuffs", "waistbands", "containment flaps" and the like, indicating their role in keeping bodily exudates within the product and so protecting the clothing, bedding, etc., from being soiled.

While currently available leg cuffs, waistbands, etc., function relatively well, there remains a need for personal care products that provide a greater degree of protection to the wearer. It is an object of the invention, therefore, to provide a personal care product that conforms and adheres to the body for increased leakage protection

SUMMARY OF THE INVENTION

The objects of the invention are achieved by a disposable personal article made with a polymer having a glass transition temperature ranging between 25 and 45° C. A preferred polymer has a main chain, lateral perfluoroalkyl groups and lateral alkyl groups. This polymer is preferably applied to a sealing surface of the article to aid in keeping any bodily exudates within the product and so avoid soiling the clothing or bedding of the wearer, as well as to seal contaminates out so that they do not contact the wearer.

BRIEF DESCRIPTION OF THE DRAWING

The FIGURE is an example of a personal care product; in this case a diaper 1, having leg cuffs 2, an elastic waistband in front 3 and rear 4 either side of the central portion 6.

DETAILED DESCRIPTION

Typical personal care product structures include a top sheet, surge layer, absorbent core and impervious backsheet.

The top sheet material is the layer against the wearer's skin and so the first layer in contact with liquid or other exudate from the wearer. The top sheet further serves to isolate the wearer's skin from the liquids held in an absorbent structure and should be compliant, soft feeling and non-irritating. Various materials can be used in forming the bodyside top sheet of the present invention, including apertured plastic films, woven fabrics, nonwoven webs, foams and the like.

An optional surge layer may be interposed between and in intimate, liquid communicating contact with the top sheet and another layer. Various foams and woven and nonwoven webs are used to construct a surge layer, and there may be a number of surge layers of different fiber size, basis weight, etc. For example, the surge layer may be a nonwoven fabric layer composed of a meltblown or spunbond web of polyolefin filaments. The surge layer also can be a bonded-carded web or an airlaid web composed of natural and/or synthetic fibers. Exemplary surge materials may be found in U.S. Pat. Nos. 5,879,343 and 5,820,973 to Dodge et al.

The layer most typically placed below the surge layer is the retention or absorbent core layer. This layer is usually made from wood pulp and/or superabsorbent particles. Pulps include standard soft-wood fluffing grade such as CR-1654 from Coosa Mills of Coosa, Ala. and high bulk additive formaldehyde free pulp (HBAFF) available from the Weyerhaeuser Corporation of Tacoma, Wash. Another useful pulp is a chemically cross-linked pulp fiber such as Weyerhaeuser NHB-416. Useful particulate superabsorbents are available from the Dow Chemical Company of Midland Mich., and the Stockhausen Company of Greensboro, N.C. 27406 (e.g., FAVOR® 870 superabsorbent) as well as others.

The backsheet is sometimes referred to as the outer cover and is the farthest layer from the wearer. The outer cover is typically formed of a thin thermoplastic film, such as polyethylene film, which is substantially impermeable to liquid. The outer cover functions to prevent body exudates contained in an absorbent structure from wetting or soiling the wearer's clothing, bedding, or other materials contacting the personal care product. The outer cover may be, for example, a polyethylene film having an initial thickness of from about 0.5 mil (0.012 millimeter) to about 5.0 mil (0.12 millimeter). The polymer film outer cover may be embossed and/or matte finished to provide a more aesthetically pleasing appearance. The outer cover may optionally be composed of a vapor or gas permeable, microporous "breathable" material, that is permeable to vapors or gas yet substantially impermeable to liquid. Additionally, the backsheet may be a laminate of materials designed to have multiple functions.

In order to prevent leakage of fluids from disposable personal articles, various safeguards have been added to them. As shown in the FIGURE, in the case, for example, of a diaper 1, there are leg cuffs 2, a waistband in front 3 and rear 4 and containment flaps 5 on either side of the central portion 6. Similar features are present in disposable swimwear, training pants and adult incontinence items. These items are designed to have a sealing surface against the skin to hold waste within the diaper and prevent soiling of the wearer's clothing. These items are usually elastic or have elastic components to aid in maintaining them against the wearer's skin. Quite effective sealing is maintained with these approaches, but there are occasional problems because of the loss of sealing. A better seal would make this system even more effective.

The inventor has found that the presence of a polymer designed to adhere and conform to the skin of the wearer forms an improved seal. The polymer may be coated onto a substrate as a liquid by spraying, dipping and the like. It may be spun into a fiber by conventional fiber forming means and mixed with the fibers from which the item is made. It may be applied as a film and bonded to the item thermally or mechanically with heat, needling, entangling and the like. In short, any effective means of delivering the polymer to the item, most preferably on the sealing surface, may be used.

The polymer to be used has a glass transition temperature (Tg) such that it becomes tacky or slightly sticky at body temperatures but loses this property at other temperatures.

The requisite Tg is between 25 and 45° C. (77 and 113° F.), and more preferably between 25 and 37° C. (77 and 98.6° F.). The glass transition temperature, sometimes referred to as the second order transition temperature, is the temperature at which the non-crystalline (amorphous) portions of a polymer begin to melt or become plastic. The preferred polymer has a main chain, perfluorinated lateral groups and alkyl lateral groups.

The main chain of the preferred polymer serves as the backbone of the structure and many chains may function appropriately. Possible main chains include polysiloxane, poly(meth)acrylic, polyvinyl, polystyrene, polyester, polyphosphazene, polyamine, poly(meth)acrylamide and polyolefin.

The perfluorinated lateral groups of the preferred polymer are attached to the main chain of the polymer by a divalent group $—(CH_2)_{m-}$, where m is a whole number between 1 and 12, preferably 2. The length of the perfluorinated groups is from 5 to 20 carbon atoms, preferably 7 to 15.

The alkyl groups of the preferred polymer have a length between 12 and 30 carbon atoms, preferably between 14 and 20.

A further description of a suitable polymer may be found in patent publication WO 99/06495 to Leibler, et al., assigned to Elf Atochem SA of France and claiming priority from PCT application 97/09778, filed Jul. 31, 1997. This publication describes the use of the polymer on handles of various types of sporting equipment, most preferably golf clubs. The amount of polymer to be used in these applications is between 0.05 and 100 g/m² and preferably between 0.25 and 20 g/m² of the surface area of the handle. The handles are grasped with the hand and, because the tackiness is in response to heat from the body, do not become dirty from dirt and dust adhering to the polymer when not in use since the polymer is not tacky when not at the proper temperature. WO 99/064595 contains no teaching or suggestion to use this polymer in personal care products.

The polymers of WO 99/064595 are taught to have a tack energy at 35° C. of between 1 and 1000 J/m² and more preferably between 10 and 100 J/m².

A particular embodiment of the polymer in which m=10 may be found in U.S. Pat. No. 5,641,844 to Thompson et al. which is assigned to WL Gore & Associates, Inc. of Newark DE, and which is incorporated by reference. This patent teaches the use of such polymers to improve water repellence.

When used in a disposable personal article the polymer is preferably located on a perimeter sealing component, as described above, so that it can seal the product against the wearer's skin. The polymer may also be advantageously located in other components of the personal care product, provided it is near enough to the wearer so that the polymer may reach its glass transition temperature. The use of the polymer in non-skin contacting areas is that are close enough to the body to reach the glass transition temperature may be, for example, in an interior layer of a laminate used as a component like the leg cuff or the backsheet. In such cases the reaching of the glass transition temperature will produce reduced flexural resistance in the laminate, hence enabling better, yet non-adhesive, conformance to the body of the wearer.

In another disposable personal article application; a bandage, for example, the polymer may be located around the absorbent pad. The bandage will adhere well to the skin because of the tacky nature of the polymer at body temperatures. When it is desired to remove the bandage, it may be painlessly removed by applying ice to the bandage to cool the polymer. When the polymer temperature drops below the prescribed lower Tg limit of 25° C., the polymer will lose its tackiness and be easily removed from the skin with little effort.

When used in a facemask, the polymer may be located on the areas most likely to contact the face of a wearer, generally the periphery of the mask, in order to improve adhesion with the face and so create a better seal. Facemasks may be used in medical applications and may also be used in industrial, commercial or residential applications. While the applications may be varied, the common purpose is generally to prevent the entry of dust and liquids into the mask so that they will not contact the skin or be breathed by a wearer.

The degree of tackiness of the polymer may be varied by adjusting the lateral groups. This may be done in the process of production of the polymer and is within the understanding and ability of those skilled in the art, without undue experimentation. The degree of tackiness will most likely be different for different products based on the surface area of the article in contact with the skin as well as the presence or absence of other mechanisms to hold the article in place. One could surmise, for example, that polymers used in bandages would need to be tackier than those used in diapers, training pants and the like. This is because the bandage must not only seal the article, but also attach the article to the wearer, whereas diapers and the like generally have a separate, non-temperature dependent, mechanical system to attach the article to the wearer. One skilled in the art may determine the tackiness and effective amount of polymer to be used based on the application as well as the particular polymer chosen.

As will be appreciated by those skilled in the art, changes and variations to the invention are considered to be within the ability of those skilled in the art. Such changes and variations are intended by the inventors to be within the scope of the invention.

What is claimed is:

1. A disposable personal article comprising a polymer having a glass transition temperature ranging between 25 and 45° C., said polymer located on a surface of said disposable personal article, such that it can aid in sealing the product against the skin of a wearer of such article during use, and/or in a position within the disposable personal article such that said polymer is near to the body of the wearer of said disposable personal article, such that the polymer may reach its glass transition temperature during use of said article.

2. The disposable personal article of claim 1 wherein said polymer has a glass transition temperature ranging between 25 and 37° C.

3. The disposable personal article of claim 1 wherein said polymer has a main chain, lateral perfluoroalkyl groups and lateral alkyl groups.

4. The disposable personal article of claim 3, wherein said perfluorinated lateral groups are attached to the main chain of the polymer by a divalent group $—(CH_2)_{m-}$, where m is a whole number between 1 and 12.

5. The disposable personal article of claim 4 wherein said perfluorinated lateral groups have a length from 5 to 20 carbon atoms.

6. The disposable personal article of claim 5 wherein said perfluorinated lateral groups have a length from 7 to 15 carbon atoms.

7. The disposable personal article of claim 3 wherein said main chain is selected from the group consisting of polysiloxane, poly(meth)acrylic, polyvinyl, polystyrene, polyester, polyphosphazene, polyamine, poly(meth)acrylamide and polyolefin.

8. The disposable personal article of claim 1 where in said polymer has a tack energy at 35° C. of between 1 and 1000 J/m$^2$.

9. The disposable personal article of claim 1 wherein said polymer is applied to a sealing surface in an amount between 0.05 and 100 g/m$^2$.

10. The disposable personal article of claim 1 selected from the group consisting of diapers, training pants, and adult incontinence products.

11. The disposable personal article of claim 1 which is a feminine hygiene product.

12. The disposable personal article of claim 1 selected from the group consisting of facemasks, bandages and wound care articles.

13. The disposable personal article of claim 4 wherein m is 2.

* * * * *